United States Patent [19]

Cimaglia et al.

[11] Patent Number: 4,989,463
[45] Date of Patent: Feb. 5, 1991

[54] SAMPLE COLLECTION SHIELD

[75] Inventors: Karen A. Cimaglia, Henderson; Jill M. Griffin, Las Vegas, both of Nev.

[73] Assignee: Kerr-McGee Chemical Corporation, Oklahoma City, Okla.

[21] Appl. No.: 487,106

[22] Filed: Mar. 2, 1990

[51] Int. Cl.⁵ .............................................. G01N 1/00
[52] U.S. Cl. ..................................... 73/863.86; 141/97
[58] Field of Search ........... 73/863.11, 863.71, 863.72, 73/863.81–863.86, 864.33, 864.34, 864.35, 864.73; 312/1, 3, 4, 209, 211, 229, 234, 237; 422/104; 141/97; 98/115.3

[56] References Cited

U.S. PATENT DOCUMENTS 2,127,296  8/1937  Holmes .
2,154,529  4/1939  Raymond .
2,513,953  11/1950  Smith et al. .
3,858,449  1/1975  Singer ............................ 73/863.83
4,014,658  1/1977  Arendsen et al. .
4,628,749  12/1986  Rafter, Jr. ....................... 73/863.71
4,736,637  4/1988  Stock .
4,791,821  12/1988  Spencer .
4,820,000  4/1989  Jacobson ............................ 312/3

Primary Examiner—Robert R. Raevis
Attorney, Agent, or Firm—Herbert M. Hanegan

[57] ABSTRACT

A sample shield for safely collecting a sample of fluid, such as a process liquor in a chemical processing plant is disclosed. The shield is constructed as an enclosure with one open side for access and the discharge outlet of a valved sampling line extend into the enclosure. The walls of the enclosure are transparent to make the sample collection process highly visible yet to provide appropriate protection to the sample taker against splashing and the like.

17 Claims, 1 Drawing Sheet

U.S. Patent  Feb. 5, 1991  Sheet 1 of 1  4,989,463
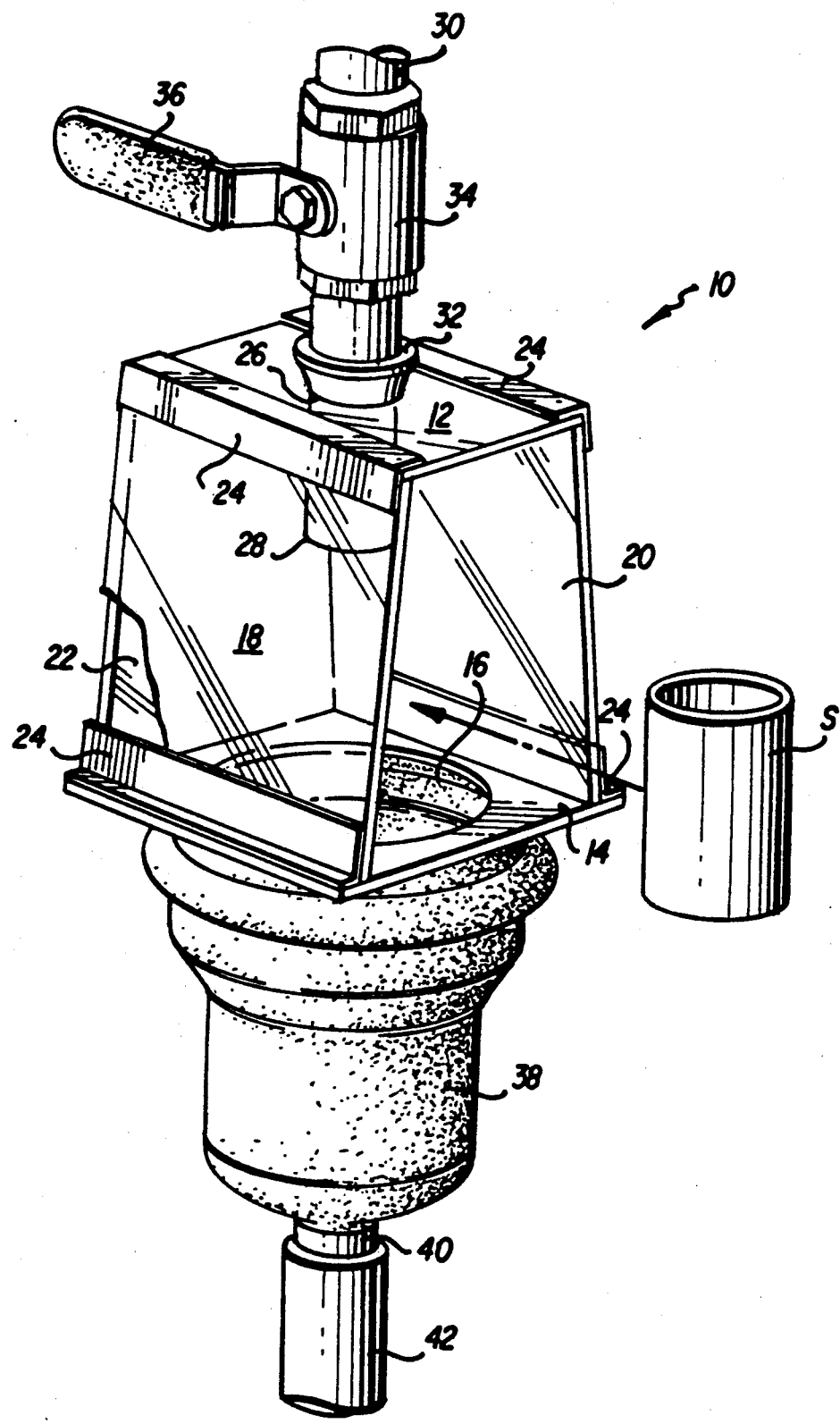

SAMPLE COLLECTION SHIELD

FIELD OF THE INVENTION

The present invention relates to sampling devices, and more particularly to a shield device for safely taking process liquor samples from a flow line in a chemical plant.

DESCRIPTION OF THE PRIOR ART

In many chemical plants and processes, it is necessary to take samples of chemicals being made or used in the chemical process, such as a process liquor sample, without exposing the personnel taking the samples to the risk of bodily contact with the chemical. Heretofore, the personnel involved in taking such chemical samples were provided with extensive equipment for protecting themselves from bodily exposure to the chemicals. Protective equipment for the body, including face shields or splash goggles, gloves, chemically resistant clothing and the like have been frequently used to prevent or minimize chemical exposure when taking chemical samples. Such equipment is often cumbersome, uncomfortable and inconvenient for the wearer and must be replaced or repaired should it become lost or misplaced, torn or otherwise damaged. Moreover, protective equipment for the entire body is costly to procure and maintain.

It is known in the art to provide enclosures for taking or handling samples of hazardous liquids or solutions. Examples of patented sample taking or handling devices are disclosed in U.S. Pat. Nos. 2,127,296; 2,154,529; 2,531,953; 4,736,637; and 4,791,821, the disclosures of which are incorporated herein by reference.

U.S. Pat. No. 4,791,821 to Spencer discloses a sample injection device for taking a sample of a hazardous material from a process line by flowing the material through a sample line past a valve and into a transparent bottle. During sample taking, the sample bottle is completely enclosed in a capped opaque shroud with a series of inspection ports to aid in preventing overfilling of the bottle.

U.S. Pat. No. 2,127,296 to Holmes discloses a sample box used for sampling a tank of crude petroleum which comprises an enclosure into which valved sample pipes are directed. A downwardly opening hinged door is provided on the front of the sample box for accessing the box interior. A perforated plate divides the box and serves as a shelf upon which sample containers may be placed in the upper part of the box. The lower part of the box serves as a drain to return to the tank any oil from the sample that may drip through the perforated plate.

The prior art sampling devices typified by those disclosed in the Spencer and Holmes patents are either overly complex for many applications as in Spencer or do not provide the necessary splash protection as in Holmes. Moreover, it is imperative that the person taking a sample from a valved chemical flow line have a substantially unobstructed view of the chemical sample as it is discharged from the flow line and into the sample container to prevent overflow of the container.

SUMMARY OF THE INVENTION

It should be apparent from the foregoing that there still exists a need in the art for a sample collection device for sampling the process liquor of a chemical process which is simple and efficient to use without the need for cumbersome protective face shields and clothing, yet provides a sufficiently safe, splash-free environment for sample taking personnel to avoid bodily contact with the chemical being sampled.

Another advantage of the present invention is the provision of a permanently installed sample collection shield which is convenient to use with a valved chemical flow line and permits a substantially unobstructed, yet well-protected field of vision of the sample discharge outlet and container during the sampling procedure.

A further advantage of the invention is the simplicity of the design of the sample shield which has no moving parts and can be easily retrofitted to existing sample collection stations in chemical process plants.

The foregoing advantages are achieved according to the invention by providing a permanently mounted shield enclosure into the top of which the discharge outlet of a sample flow line of a chemical process is inserted. The bottom of the enclosure opens into a collection funnel which discharges into a process drain via a pipe. The enclosure has four sides, one of which is open and three of which are enclosed by walls or panels. At least one panel, preferably the front panel, is transparent, but all three panels may be transparent to improve the visibility and light transmission into the interior of the enclosure. The front panel is preferably inclined rearwardly from bottom to top to also improve the visibility inside the enclosure during the sample taking procedure. The valve in the sample flow line is preferably positioned in the line immediately above the top of the shield enclosure so that it is conveniently accessible to the person taking the sample. Transparent Plexiglas has been found suitable for the transparent walls of the shield in some chemical process applications, however, any other suitable transparent plastic or glass material may be used. Silicone rubber has also be found suitable in some chemical processes for sealing the edges of the enclosure and the connections between the enclosure and the flow line and collection funnel.

The open side of the enclosure is provided for access to the interior of the enclosure by the person or operator taking the sample. Ordinarily, the operator will cover the hand holding the sample container with a protective glove or mitt leaving the other hand, which may be ungloved, free to manipulate the valve in the sample flow line immediately above the shield enclosure.

These and other features and advantages of the invention will be apparent from the following detailed description of the invention taken in conjunction with the accompanying drawing.

BRIEF DESCRIPTION OF THE DRAWING

The sole drawing figure is a perspective view of a preferred embodiment of the shield enclosure of the invention with a portion broken away to show a portion of a hidden side of the enclosure.

DETAILED DESCRIPTION OF A PREFERRED EMBODIMENT

Referring now to the drawing, the sample shield enclosure of the invention is shown in perspective view and is designated generally by reference numeral 10. The shield 10 is a box-like enclosure having a rectangular top plate 12 and a rectangular bottom plate 14 with a central circular opening 16 therein. The walls of the shield 10 comprise a front panel 18, a rear panel 20, and a side panel 22. The side of the shield opposite side panel 22 is completely open to provide access for a sample container S in the direction shown by the arrow in the drawing. As shown in the drawing, the open side of the shield is defined by a free edge of each of the top plate 12, the bottom plate 14, the front panel 18 and the rear panel 20. Preferably, the top plate 12, front panel 18, rear panel 20 and side panel 22 are made of a transparent plastic sheet material, such as Plexiglas, and the bottom plate is made of metal or plastic.

The shield enclosure may be assembled in any suitable way, for example, by fastening the enclosure components or panels together with metal (e.g., stainless steel) brackets 24 and a bonding agent or with other types of fasteners, such as bolts, screws or the like (not shown). Preferably, the mating edges of the enclosure panels are sealed with a sealant, such as silicone rubber or another sealant compatible with the chemical being sampled.

An opening 26 is provided in the top plate 12 for insertion of the discharge or outlet end 28 of a chemical sampling line 30. A seal or grommet 32 is provided to seal between the outlet end 28 and the opening 26 in the top plate. Silicone rubber may also be used for this purpose. A stainless steel ball valve 34 with an operating handle 36 is provided in the sampling line 30 outside the shield enclosure and immediately above the top plate 12.

Beneath the opening 16 in the bottom plate 14 a collection funnel 38 is positioned to catch chemical drippings or splashing from the outlet end 28, or overflow from the sample container S. The collection funnel 38 is preferably made of high density polyethylene or other suitable plastic and is sealed to the underside of the bottom plate 14 around opening 16 by means of silicone rubber or other sealant. The funnel 38 has a drain 40 to which is connected to a process drain pipe 42.

As shown, the front panel 18 is preferably inclined rearwardly from bottom to top to improve the visibility of the sample taking procedure within the enclosure. Although it is only necessary to provide sufficient visibility of the enclosure interior to render the sample taking procedure safe, e.g., by making only the front panel 18 transparent, it is advantageous to make all the panels 18, 20, 22 and the top plate 12 transparent to provide as much light and visibility as possible within the interior of the enclosure.

The rear panel 20 may be arranged at right angles to the bottom plate 14 or it may also be inclined in the same manner as the front panel 18. If the rear panel 20 is also inclined both right-handed and left-handed operators will find operation of the sample taking device of the present invention very convenient. It may also be advantageous to provide valve handles 36 on both sides of the ball valve 34 for use by right- and left-handed operators.

Operation of the sample taking device will now be described. Assuming a right-handed operator must collect a chemical sample, the operator will first glove his or her right hand and firmly grasp the sample container S with the gloved hand. The operator then stands in front of the front panel 18, preferably toward the left-hand side thereof, or if practicable in front of the side panel 22, and with the right, gloved hand inserts the sample container S into the shield enclosure beneath the outlet end 28. Then, with the left hand, which may be ungloved, the operator actuates the valve handle 36 to open the ball valve 34 and introduce into the container S an appropriate volume of a chemical sample, such as a process liquor. The positioning of the operator's hands, one inside the enclosure, and one on the valve handle above the enclosure, also makes it necessary for the operator to stand relatively upright, thereby also helping to keep the operator's face away from the potential splash zone of the sampling procedure.

The transparent shield 10 provides excellent visibility for taking the sample and prevents any chemical splashes from contacting the unprotected parts of the operator's body, such as the face or ungloved left hand.

Those skilled in the art will appreciate that a left-handed operator would be able to collect a sample in the same safe environment by standing on the opposite side of the shield 10 in front of the rear panel 20. Since the shield enclosure is permanently mounted, reliance on protective clothing (other than a protective glove) is not necessary and compliance with safety procedures by the operator is more likely.

Although only a preferred embodiment of the invention has been described herein, it will be apparent to those skilled in the art to which the invention pertains that variations and modifications of the described embodiment may be made without departing from the true spirit and scope of the invention. Accordingly, it is intended that the invention be limited only to the extent required by the appended claims and the applicable rules of law.

What is claimed is:

1. A sample shield for use in taking a fluid sample from a sampling line having a valve and a discharge outlet, said shield comprising:
   a shield enclosure into which the discharge outlet of the sampling line is inserted, said enclosure having a plurality of panels in fixed, immovable positions relative to one another, at least one of said panels being transparent to permit visual observation of the sample taking procedure;
   means providing one open side of said enclosure for freely accessing the discharge outlet of the sampling line during the taking of a sample such that a fluid sample can be taken from the discharge outlet and removed from the enclosure without moving any of said panels of the enclosure.

2. The sample shield according to claim 1, wherein said plurality of panels includes top and bottom walls, front and rear walls and one side wall, at least the top, front, rear and one side wall being transparent.

3. The sample shield according to claim 1, wherein said transparent panel has upper and lower edges, said panel being inclined inwardly toward the interior of the enclosure and, from the lower edge to the upper edge of the panel to improve the visibility of the interior of the enclosure.

4. The sample shield according to claim 1, wherein said transparent wall is made of a plastic or glass material.

5. The sample shield according to claim 1, wherein said plurality of panels includes a top and bottom wall, the discharge outlet passing through the top wall, said bottom wall having an opening therein, and a collection funnel connected to the bottom wall beneath the opening therein.

6. The sample shield according to claim 5, wherein said funnel has an outlet and a drain line connected to the funnel outlet.

7. The sample shield according to claim 5, including a front, rear and a side wall.

8. The sample shield according to claim 7, wherein said front wall is transparent and is inclined toward the rear wall from the bottom wall to the top wall.

9. The sample shield according to claim 8, wherein said top, front, rear and side walls are transparent.

10. The sample shield according to claim 7, wherein said front and rear walls are both transparent and are inclined toward one another from the bottom wall to the top wall.

11. The sample shield according to claim 10, wherein said top, front, rear and side walls are transparent.

12. The sample shield according to claim 7, wherein said top, front, rear and side walls are transparent.

13. The sample shield according to claim 12, wherein said transparent walls are made of a plastic or glass material.

14. The sample shield according to claim 7, including a sealant disposed between the walls of said enclosure, between the discharge outlet and the top wall and between the collection funnel and the bottom wall.

15. The sample shield according to claim 1, wherein said valve is located on the exterior of said shield enclosure.

16. A sample shield for use in taking a fluid sample from a sampling line having a valve and a discharge outlet, said shield comprising a shield enclosure into which the discharge outlet of the sampling line is inserted, said enclosure comprising a top wall and a bottom wall and only three side panels, at least one of which is transparent to permit visual observation of the sample taking procedure, said top and bottom walls and said three side panels being in fixed immovable positions relative to one another, said top and bottom wall and at least two of said side panels each having a free edge, said at least two side panels being inclined toward one another from the bottom wall to the top wall, means providing one open side of said enclosure for freely accessing the discharge outlet of the sampling line such that a fluid sample can be taken from the discharge outlet and removed from the enclosure without moving any of said side panels of the enclosure, said means being defined by the free edges of the top and bottom walls and the free edges of said at least two side panels, said free edges being unconnected to any other panel or wall.

17. The sample shield of claim 16, wherein said three side panels are all transparent.

* * * * *